United States Patent [19]

Maurin, III

[11] 4,418,232

[45] Nov. 29, 1983

[54] DEHYDROHALOGENATION PROCESS

[75] Inventor: Louis J. Maurin, III, Wilmington, Del.

[73] Assignee: E. I. Du Pont de Nemours & Co., Wilmington, Del.

[21] Appl. No.: 445,155

[22] Filed: Nov. 29, 1982

[51] Int. Cl.$^3$ ............................................. C07C 17/34
[52] U.S. Cl. ..................................... 570/228; 570/229
[58] Field of Search ................................ 570/228, 229

[56] References Cited

U.S. PATENT DOCUMENTS 3,754,044  8/1973  Hargreaves et al. ............... 570/228
3,981,937  9/1976  Campbell et al. .................. 570/228

Primary Examiner—Charles F. Warren
Assistant Examiner—Joseph A. Boska

[57] ABSTRACT

Improvement in the catalytic dehydrohalogenation of a halogenated hydrocarbon to an ethylenically unsaturated product with aqueous alkali in a series of reactors in a cascade arrangement, wherein the fresh alkali feed is relocated from the first reactor to a reactor subsequent to the first, and partly spent alkali solution from the last reactor is recirculated to the first reactor, while the ethylenically unsaturated product is recovered from the effluent from the last reactor, and waste brine is removed from the effluent from the reactor immediately preceding that to which fresh alkali is fed. In this manner, the amount of both the alkali and the catalyst can be reduced, and the conversion is increased. Dehydrochlorination of 3,4-dichlorobutene-1 gives chloroprene, which is a valuable monomer for making synthetic elastomers.

8 Claims, 3 Drawing Figures

4,418,232

DEHYDROHALOGENATION PROCESS

BACKGROUND OF THE INVENTION

This invention relates to an improvement in the process for dehydrohalogenating a halogenated hydrocarbon to an ethylenically unsaturated product in the presence of a phase-transfer catalyst.

The term "phase-transfer catalysis" describes reactions between reactants located in different phases brought about by the use of small quantities of an agent which transfers one reactant across the interface into the other phase so that the reaction can proceed. The phase-transfer agent is not consumed but performs the transport function repeatedly. See Starks, *J. Am. Chem. Soc.* 93:1, 195 (1971) and Starks et al. *J. Am. Chem. Soc.* 95:11, 3613 (1973). Also see U.S. Pat. No. 3,992,432 (to Napier et al.) and a book by Starks et al, entitled "*Phase-Transfer Catalysis*", Academic Press, New York, N.Y. 1978. The first paper in the above series considers organic-soluble quaternary ammonium and phosphonium ions to be excellent agents for the transport of anions from aqueous phase to an organic phase. Such quaternary ions thus are effective phase-transfer catalysts in reactions in which anions participate, for example, in displacement reactions.

A typical catalytic dehydrohalogenation process is described in U.S. Pat. No. 3,981,937 to Campbell et al., wherein 3,4-dichlorobutene-1 (sometimes hereafter abbreviated to DCB) is dehydrochlorinated with aqueous alkali to 2-chlorobutadiene-1,3 (also known as chloroprene). The catalyst is a quaternary ammonium chloride but can also be another phase-transfer catalyst; see, for example, U.S. Pat. Nos. 3,639,492, 3,639,493, and 3,876,716 (all to Campbell).

In the industrial practice of this process, the dehydrochlorination is often carried out in a series of continuous stirred-tank reactors, the initial stages being cooled to remove the heat of the reaction. DCB, the catalyst, and an excess of aqueous NaOH are fed into the first reactor, where much of the reaction takes place. As the reactants become depleted, the reaction rate decreases, so that a large proportion of the total reactor volume is required to complete the last few percent of the reaction. Crude chloroprene is recovered from the effluent of the last stage; aqueous and organic phases are separated, and waste organics and waste brine are disposed of.

It is desirable to improve the reactor utilization in the chloroprene manufacturing process and in similar dehydrohalogenation processes so that better process economy can be achieved.

SUMMARY OF THE INVENTION

According to this invention, there is provided in a process for dehydrohalogenating a halogenated hydrocarbon to an ethylenically unsaturated product with aqueous alkali in the presence of a phase-transfer catalyst in a series of at least two liquid-full reactors operating in a cascade arrangement, the improvement of feeding the halogenated hydrocarbon and the catalyst to the first reactor while feeding fresh aqueous alkali to a reactor subsequent to the first, which aqueous alkali may be fed together with the organic phase entering that reactor, separating the effluent from the last reactor into a partially spent aqueous alkali solution, which is fed to the first reactor, and an organic phase, from which the resulting ethylenically unsaturated product is recovered; and removing waste brine from the effluent from the reactor immediately preceding the fresh aqueous alkali feedpoint.

DETAILED DESCRIPTION OF THE INVENTION

Any saturated or unsaturated halogenated hydrocarbon which can be dehydrohalogenated with aqueous alkali in the presence of a phase-transfer catalyst is a suitable starting material in the process of this invention. Particularly important are 1,2,3,4-tetrachlorobutane, 3,4-dichlorobutene-1, and 2,3,4-trichlorobutene-1. Other starting halogenated hydrocarbons include, for example, 2,3-dichlorobutane, 2-bromoethylbenzene, 1,2-dichloroethane, 1,2-dibromoethane, and chlorocyclohexane.

The description of the catalytic DCB dehydrochlorination processes of U.S. Pat. Nos. 3,981,937, 3,639,492, 3,639,493, and 3,876,716 is herein incorporated by reference. All manner of phase-transfer catalysts disclosed in the above patents are suitable in such a process, but the preferred catalysts are quaternary ammonium salts, especially quaternary ammonium chlorides, particularly those represented by the formula $R^1R^2R^3R^4NCl$ in which each of $R^1$, $R^2$ and $R^3$ independently is a $C_1$–$C_{20}$ alkyl, a $C_2$–$C_{20}$ alkenyl, or a $C_7$–$C_{20}$ aralkyl, and $R^4$ is a $C_6$–$C_{20}$ alkyl or alkenyl, benzyl, or a ($C_6$–$C_{20}$) alkyl- or alkenyl-substituted benzyl. Each of $R^1$, $R^2$, and $R^3$ groups in these quaternary ammonium chlorides may also contain a hydroxyl or ether group in a position beta to the nitrogen atom. The amount of the quaternary ammonium compound is about 0.01–10% by weight of the starting halogenated hydrocarbon.

Other suitable phase-transfer catalysts include quaternary phosphonium salts and sulfonium salts having their respective formulas $R^1R^2R^3R^4PX$ and $R^1R^2R^3SX$ in which X is the anion, and $R^1$, $R^2$, $R^3$, and $R^4$ have the same meaning as above.

The alkali can be any alkali, such as sodium hydroxide, potassium hydroxide, or calcium hydroxide, but usually will be sodium hydroxide. The alkali normally will be used in slight excess, and the usual mole ratio of alkali to DCB will be approximately 1.001 to 1.3, but this ratio is not critical.

Although the minimum number of reactors (stages) employed in the process of this invention is two, a larger number may be preferred. The reactors preferably are made of or lined with a corrosion-resistant material, such as, for example, nickel. They are provided with adequate heating and cooling means and with an agitating means.

Figure 1:
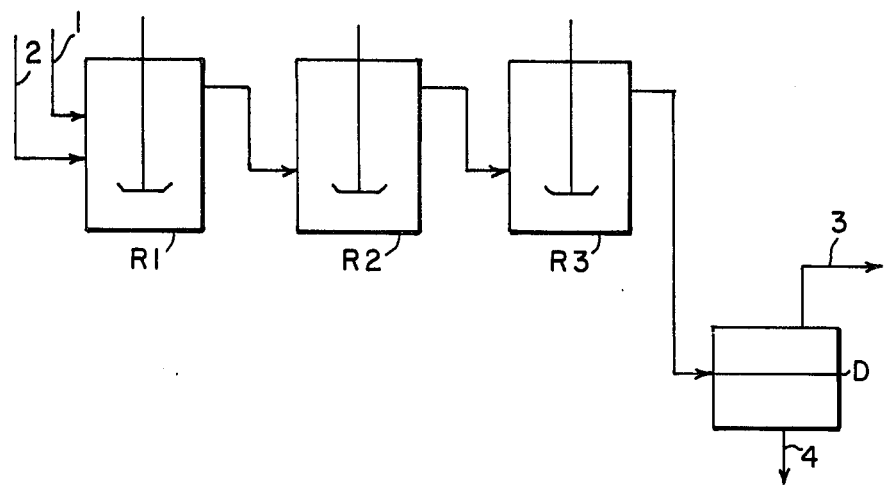
FIG. 1 is a schematic diagram of a prior art conventional process employing several reactors in a cascade arrangement.
Figure 2:
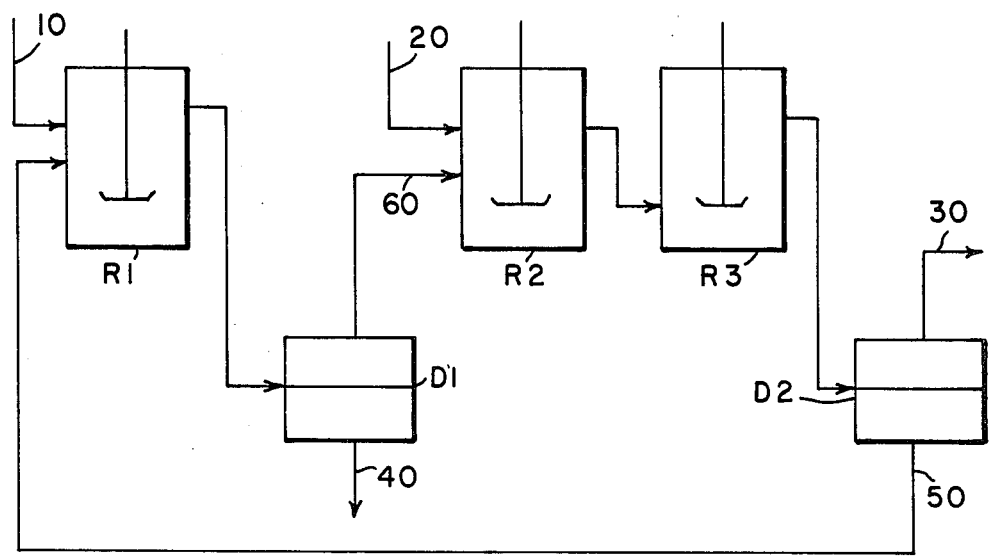
FIG. 2 is a schematic diagram of one of the embodiments of the process of the present invention.
Figure 3:
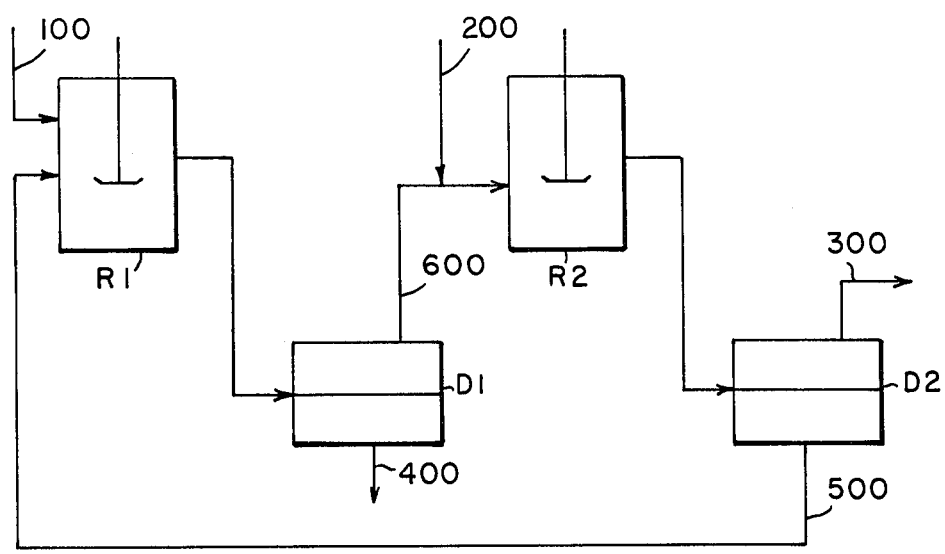
FIG. 3 is a schematic diagram of another embodiment of the instant process, where only two reactors are employed.

The improved process of the present invention can be well understood by comparing FIGS. 2 and 3 with FIG. 1. In a conventional prior art process, represented by FIG. 1, the dehydrohalogenation is carried out in several stages, which are here shown as reactors R1, R2 and R3. A mixture of catalyst with the starting halogenated hydrocarbon is fed to R1 through line 1, and aqueous alkali is fed through line 2. The effluent from each stage is fed to the next stage, and the effluent from the last stage is separated into the organic phase and the aqueous phase in decanter D. The ethylenically unsaturated product is recovered from the organic phase removed through line 3, and waste brine is removed through line 4.

Referring now to FIG. 2, which illustrates one embodiment of the process of the present invention, a mixture of catalyst with the halogenated hydrocarbon, for example DCB, is fed through line 10 to the first stage, R1. Fresh aqueous alkali solution is fed to reactor R2 through line 20. The effluent from R2 is introduced to reactor R3, and the effluent from R3 is separated into phases in decanter D2. The ethylenically unsaturated product, for example, chloroprene, is recovered from the organic phase, which is removed through line 30, while the aqueous phase containing a mixture of sodium hydroxide and sodium chloride is fed through line 50 to the first stage. The effluent from R1 is separated in decanter D1 into the organic phase containing in the exemplary case a mixture of DCB and chloroprene and the aqueous phase, which is waste brine. The organic phase is fed through line 60 to stage R2, and waste brine is removed through line 40.

FIG. 3 shows schematically a two-reactor process of the present invention. A mixture of catalyst with the halogenated hydrocarbon is fed through line 100 to the first stage, R1. Fresh aqueous alkali solution fed through line 200 is combined in line 600 with the upper phase from decanter D1 containing a mixture of unchanged starting halogenated hydrocarbon (e.g., DCB) and ethylenically unsaturated product (e.g., chloroprene). The combined two-phase mixture is introduced into reactor R2, and the effluent from reactor R2 is separated into phases in decanter D2. Alternatively, fresh aqueous alkali solution can be fed directly to reactor R2 in the manner shown in FIG. 2. The organic phase, which is removed through line 300, contains mainly the ethylenically unsaturated product. The aqueous phase, consisting of a mixture of alkali metal hydroxide and brine, is fed to reactor 1 via line 500. The waste brine removed through line 400 from the bottom of decanter D1, which is fed the effluent from reactor R1, is disposed of.

The process of the present invention results in a higher conversion of halogenated hydrocarbon to ethylenically unsaturated product than does the conventional process. At the same time, less catalyst and alkali are required than in the conventional process because the reaction driving forces are spread more evenly throughout the existing reactor volumes, thus resulting in considerable savings. These improvments are obtained for any number of reactors arranged in series. The preferred location of fresh alkali feed is about the midpoint of the reactor train; however, most of the benefits of this invention will also be realized when the fresh alkali solution is fed to some other stage between the first reactor and the last. Except for the relocation of the various feed and recovery streams, and reduction in alkali and catalyst flows, other process conditions, such as the temperature and flow rates, are substantially the same as in the past.

This invention is now illustrated by the following examples of certain representative embodiments thereof, where all parts, proportions, and percentages are by weight unless otherwise indicated.

EXAMPLE 1

In this example, run A was made according to the prior art process shown in FIG. 1, while run B was made according to the present process. In each case, three back-mixed 1650 mL nickel reactors were used. DCB containing 2500 ppm of catalyst, cocobenzyl-bis($\beta$-hydroxypropyl)ammonium chloride was fed to the first stage at a rate of 0.918 kg/hr. Fresh aqueous alkali was a 22% solution of NaOH in water. In run A, the feed mole ratio of NaOH to DCB was 1.058; in run B, the ratio was 1.064. The DCB conversion in each stage was determined for each run by gas chromatography. The results are shown in the following table:

|  | DCB Conversion, % | |
| --- | --- | --- |
|  | Run A | Run B |
| Stage 1 | 85.62 | 68.96 |
| Stage 2 | 96.03 | 99.31 |
| Stage 3 | 98.92 | 99.98 |
| Unconverted DCB at exit from Stage 3 (as % of original DCB) | 1.08 | 0.02 |

It can be seen that in run B the amount of unconverted DCB in Stage 3 is so small as to be nearly zero. This result shows that more driving force is available because of higher alkali concentration in the later stages of the reaction.

EXAMPLE 2

This example is a process simulation for a plant-size operation based on known reaction kinetics and on the use of known equipment. The operating parameters as well as the results were calculated for a process employing eight back-mixed, liquid-full reactors connected in series. The catalyst is the same as in Example 1, and the DCB feed rate is 16,589 kg/hr.

|  | Run C (comparative) | Run D (present invention) |
| --- | --- | --- |
| NaOH concentration in water, % | 22 | 20 |
| NaOH/DCB feed mole ratio | 1.115 | 1.020 |
| Catalyst concentration in DCB feed, ppm | 2420 | 1060 |
| Fresh alkali feed stage | 1 | 5 |

| | DCB Conversion, % | |
| --- | --- | --- |
| | Run | |
| Stage | C | D |
| 1 | 76.95 | 39.60 |
| 2 | 90.60 | 48.92 |
| 3 | 95.47 | 54.00 |
| 4 | 97.55 | 56.26 |
| 5 | 98.52 | 93.64 |
| 6 | 99.11 | 98.59 |
| 7 | 99.44 | 99.66 |
| 8 | 99.66 | 99.92 |
| Yield of chloroprene (%) | 99.6 | 99.7 |

The above data show that both the amount of catalyst and the excess of fresh alkali can be conveniently reduced, while the DCB conversion and yield of chloroprene are slightly increased when operating according to the process of the present invention.

EXAMPLE 3

In actual trial plant runs employing four back-mixed, liquid full reactors using the same catalyst as in Example 1, DCB was fed at the rate of 4310 kg/hr; fresh aqueous alkali was a 20.5% solution of sodium hydroxide; and the other process conditions and results were as shown below:

|  | Run E (comparative) | Run F (present invention) |
|---|---|---|
| NaOH/DCB feed mole ratio | 1.064 | 1.008 |
| Catalyst concentration in DCB feed, (ppm) | 2100 | 1115 |
| Unconverted DCB after final stage (% of original) | 0.73 | 0.22 |
| Yield of chloroprene (%) | 99.0 | 99.2 |
| Fresh alkali feed stage | 1 | 3 |

| | DCB Conversion, % | |
|---|---|---|
| | Run | |
| Stage | E | F |
| 1 | 83.9 | 56.0 |
| 2 | 95.4 | 62.3 |
| 3 | 98.3 | 97.3 |
| 4 | 99.27 | 99.78 |

Here again the amounts of both sodium hydroxide and catalyst were reduced, while both the DCB conversion and the yield of chloroprene were increased when the fresh alkali feed was switched from the first stage to the third stage.

I claim:

1. In a process for dehydrohalogenating a halogenated hydrocarbon to an ethylenically unsaturated product with aqueous alkali in the presence of a phase-transfer catalyst in a series of at least two liquid-full reactors operating in a cascade arrangement, the improvement of feeding the halogenated hydrocarbon and the catalyst to the first reactor while feeding fresh aqueous alkali to a reactor subsequent to the first, which alkali may be fed together with the organic phase entering that reactor, separating the effluent from the last reactor into a partially spent aqueous alkali solution, which is fed to the first reactor, and an organic phase, from which the ethylenically unsaturated product is recovered; and removing waste brine from the effluent from the reactor immediately preceding the fresh aqueous alkali feedpoint.

2. The process of claim 1 wherein the starting halogenated hydrocarbon is 1,2,3,4-tetrachlorobutane or 3,4-dichlorobutene-1.

3. The process of claim 1 wherein the catalyst is a quaternary ammonium compound.

4. The process of claim 3 wherein the catalyst is a quaternary ammonium chloride.

5. The process of claim 4 wherein the quaternary ammonium chloride has the formula $R^1R^2R^3R^4NCl$ in which each of $R^1$, $R^2$ and $R^3$ independently is a $C_1$–$C_{20}$ alkyl, a $C_2$–$C_{20}$ alkenyl, or a $C_7$–$C_{20}$ aralkyl; and $R^4$ is a $C_6$–$C_{20}$ alkyl or alkenyl, benzyl, or a ($C_6$–$C_{20}$) alkyl- or alkenyl-substituted benzyl;

with the proviso that each of $R^1$, $R^2$, and $R^3$ may also contain a hydroxyl or ether group in a position beta to the nitrogen atom.

6. The process of claim 1 wherein the number of reactors is 3 to 8.

7. The process of claim 1 wherein the alkali is sodium hydroxide.

8. The process of claim 1 wherein the location of fresh alkali feed is about the midpoint of the reactor train.

* * * * *